United States Patent
Ambrosina et al.

(10) Patent No.: US 11,446,437 B2
(45) Date of Patent: Sep. 20, 2022

(54) FLUID DELIVERY EVENT TRACKING AND TRANSACTION MANAGEMENT

(71) Applicant: Ivenix, Inc., North Andover, MA (US)

(72) Inventors: Jesse E. Ambrosina, Topsfield, MA (US); George W. Gray, North Andover, MA (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 469 days.

(21) Appl. No.: 16/440,406

(22) Filed: Jun. 13, 2019

(65) Prior Publication Data

US 2019/0381242 A1    Dec. 19, 2019

Related U.S. Application Data

(60) Provisional application No. 62/686,935, filed on Jun. 19, 2018.

(51) Int. Cl.
  *G16H 20/17*    (2018.01)
  *A61M 5/172*    (2006.01)
  (Continued)

(52) U.S. Cl.
  CPC .............. *A61M 5/172* (2013.01); *G06Q 20/10* (2013.01); *G16H 10/00* (2018.01); *G16H 10/60* (2018.01);
  (Continued)

(58) Field of Classification Search
  CPC ........ G16H 10/60; G16H 40/20; G16H 50/20; G16H 15/00; G16H 20/00; G16H 20/10;
  (Continued)

(56) References Cited

U.S. PATENT DOCUMENTS

2005/0055242 A1*  3/2005  Bello ............... G16H 20/17
                                                705/2
2008/0086086 A1*  4/2008  Field ............... G16H 20/17
                                                604/123
(Continued)

FOREIGN PATENT DOCUMENTS

WO    2018/013842 A1    1/2018

OTHER PUBLICATIONS

Griggs KN, Ossipova O, Kohlios CP, Baccarini AN, Howson EA, Hayajneh T. Healthcare Blockchain System Using Smart Contracts for Secure Automated Remote Patient Monitoring. J Med Syst. Jun. 6, 2018;42(7):130. doi: 10.1007/s10916-018-0982-x. PMID: 29876661. (Year: 2018).*

(Continued)

*Primary Examiner* — Joseph D Burgess
(74) *Attorney, Agent, or Firm* — Armis IP Law, LLC

(57)  ABSTRACT

A system includes: a fluid delivery pump and a network of multiple record management processing nodes. The fluid delivery pump is in communication with one or more of the record management-processing nodes in the network. At least a first record management processing node receives input indicating a fluid delivery event. The fluid delivery event indicates fluid delivery from the fluid delivery pump to a recipient. The record management-processing node identifies code pertinent to the fluid delivery event; the code includes criteria in which to validate the fluid delivery event. In response to validation of the fluid delivery event as specified by the criteria in the code, a resource such as the record management-processing node triggers a transaction associated with the fluid delivery event.

24 Claims, 10 Drawing Sheets

(51) Int. Cl.
  *G06Q 20/10* (2012.01)
  *G16H 10/00* (2018.01)
  *G16H 40/00* (2018.01)
  *G16H 10/60* (2018.01)
  *A61M 5/142* (2006.01)

(52) U.S. Cl.
  CPC ............ *G16H 20/17* (2018.01); *G16H 40/00* (2018.01); *A61M 2005/14208* (2013.01); *A61M 2205/3553* (2013.01); *A61M 2205/50* (2013.01)

(58) Field of Classification Search
  CPC ........ G16H 20/30; G16H 20/60; G16H 20/70; G16H 50/30; G16H 50/50; G16H 10/65; G16H 40/63; G16H 70/20; G16H 70/60; G16H 10/20; G16H 10/40; G16H 30/20; G16H 30/40; G16H 40/40; G16H 40/67; G16H 50/70; G16H 70/00; G16H 80/00; G16H 40/60; G06Q 40/08; G06Q 20/22; G06Q 20/40; G06Q 20/405; G06Q 20/36; G06Q 20/3674
  See application file for complete search history.

(56) References Cited

U.S. PATENT DOCUMENTS

| | | |
|---|---|---|
| 2010/0265072 A1 | 10/2010 | Goetz et al. |
| 2012/0039809 A1 | 2/2012 | Levinson et al. |
| 2014/0222450 A1 | 8/2014 | Gray et al. |
| 2014/0288947 A1 | 9/2014 | Simpson et al. |
| 2016/0151015 A1 | 6/2016 | Condurso et al. |
| 2017/0161439 A1 | 6/2017 | Raduchel et al. |
| 2017/0173262 A1 | 6/2017 | Veltz |
| 2018/0018590 A1* | 1/2018 | Szeto ............... G06N 20/10 |
| 2018/0211059 A1* | 7/2018 | Aunger ............ H04L 63/0428 |
| 2019/0266597 A1* | 8/2019 | Mohtar ............. G16H 10/60 |
| 2019/0355472 A1* | 11/2019 | Kutzko ............. G16H 20/10 |

OTHER PUBLICATIONS

Secure and Trustable Electronic Medical Records Sharing using Blockchain, Alevtina Dubovitskaya, Zhigang Xu, Samuel Ryu, Michael Schumacher, Fusheng Wang, AMIA 2017 Annual Symposium Proceedings, Aug. 2, 2017 (Year: 2017).*

International Preliminary Report on Patentability, PCT/US2019/036988; Dec. 22, 2020, pp. 9.

International Search Report for PCT/US2019/036988; dated Oct. 9, 2019; 2 pages 13.

EP Search Report, EP 19 823 249.8, dated Jul. 12, 2021, pp. 1-8.

Griggs Kristen N et al.: "Healthcare Blockchain System Using Smart Contracts for Secure Automated Remote Patient Monitoring",J Ournal of Medical Systems, Plenum Publishing Co. NY, USA. vol. 42, No. 7, Jun. 6, 2018 (Jun. 6, 2018), pp. 1-7, XP036532576.

Examination report No. 1 for standard application, Application No. 2019289075, Feb. 22, 2021, pp. 1-13.

* cited by examiner

FLUID DELIVERY EVENT TRACKING AND TRANSACTION MANAGEMENT

RELATED APPLICATION

This application claims the benefit of U.S. Provisional Patent Application Ser. No. 62/686,935 entitled "FLUID DELIVERY EVENT TRACKING AND TRANSACTION MANAGEMENT," filed on Jun. 19, 2018, the entire teachings of which are incorporated herein by this reference.

BACKGROUND

Many forms of healthcare require use of very sophisticated medical devices. These medical devices are adding ever-increasing levels of automation, connectivity, and mobility. Caregivers typically depend on use of the medical devices to perform respective one or more therapeutic tasks and, in certain instances, generate information associated with the one or more tasks. The generated information may be presented in one or more forms such as performance data, interaction logs, event history logs, alarms, and warnings.

Conventional medical devices may be communicatively connected to a larger hospital information system that automatically links information such as patient, provider, and care task with an electronic medical record (EMR) system, automatically updated operating software, automatically update automated decision support, etc.

Most of these device interactions (such as use of a medical device to provide healthcare) require security and a high level of data integrity. As healthcare continues to transcend the traditional physical boundaries of a hospital, such as to homes or other care settings, the need for security and data integrity are become even greater.

This disclosure includes the observation that all of the digital interactions with use of conventional medical devices present a potential vulnerability. For example, healthcare institutions and government regulators are becoming increasingly exposed to cyber-security threats. Cyber attacks occur in any manner, and tend to focus on operations such as: i) changing the operation of the device and/or the care being delivered, ii) redirecting the delivering of a medication, iii) using the device to gain access to valuable patient information or using the device to gain access to other systems within the healthcare enterprise, etc. In each case, the hacker can inflict harm on the patient and/or achieve financial gains through various means such as hacking the device to alter therapy or hacking the network to create false transactions resulting in financial to the hacker. Thus, a patient's well being may be compromised if corresponding healthcare information is not secure.

Historically a hospital network is isolated from outside threats; corresponding medical devices are physically contained within the boundaries of the hospital. A system of firewalls and security software defend the hospital network from external attacks. The fundamental weakness of this system is the centralization of both the information and the administrative authority. The same fundamental weakness of centralization plagued the fault-tolerance of early computer networks. This gave rise to the Internet, which is a distributed and decentralized network topology. Attacking any one node cannot compromise the entire system.

Blockchains provide security using a system of distributed and decentralized processing nodes that must agree on any new transaction block before it is added to the chain and accepted by the network. Since this is a distributed, "trustless" system, there is no one central or third-party authority that can be compromised. Complex mathematical algorithms ensure that there is only ever one version of the transaction history. This timestamped transaction history is often referred to as a ledger. In the context of a medical device the ledger holds a permanent record of therapeutic or device related events within a health care system.

BRIEF DESCRIPTION OF EMBODIMENTS

This disclosure includes the observation that conventional techniques of managing records and providing healthcare to a patient is a complex process.

Embodiments herein include novel approaches to tracking healthcare data and initiating transactions between one or more parties associated with providing healthcare to a patient.

More specifically, in one embodiment, a system includes a fluid delivery device and a network of multiple processing nodes that collectively manage one or more records associated with delivery of fluid to a recipient such as a patient. The fluid delivery device is in communication with one or more record management processing nodes in a network. The record management-processing nodes can be configured to individually or collectively control updating of a respective one or more records associated with the recipient or fluid delivery event.

In one embodiment, the fluid delivery device establishes a communication link between the fluid delivery device and (at least) a first record management-processing node in the network. The first record management-processing node receives, such as from the fluid delivery device itself or other resource, input indicating a fluid delivery event from the fluid delivery device. The fluid delivery event can include any suitable information. For example, in one embodiment, the fluid delivery event indicates an event of delivering fluid (such as a fluid prescribed by a doctor) from the fluid delivery device to a recipient such as a patient).

The actual notification of the fluid delivery event to the record management-processing node can include any suitable information such as a globally unique identifier value assigned to the fluid delivery device, a globally unique identifier value assigned to the patient (recipient) receiving the fluid delivery, type of fluid delivered to the recipient, date of delivery, identity of a doctor prescribing the fluid delivery to the recipient, business entity employing the doctor, etc.

The notification of the fluid delivery event to the first record management-processing node prompts the first record management-processing node to identify code (such as executable code, instructions, rules, etc.) pertinent to the fluid delivery event. In one embodiment, the one or more processing nodes in the network are operable to: receive notification of a unique identifier value assigned to the recipient; and utilize the unique identifier value to obtain the code applicable to the fluid delivery event.

In accordance with further embodiments, the code includes criteria in which to validate the fluid delivery event for possible triggering of a transaction. In response to validation of the fluid delivery event, the first record management-processing node triggers an appropriate transaction amongst one or more parties associated with fluid delivery event.

As a more specific example, in one embodiment, the criteria may indicate that the transaction (such as payment to a caregiver for administering the fluid delivery) may not take place unless criteria as specified by the code are met. The criteria may require that multiple entities associated with the fluid delivery event each provide appropriate input associated with the fluid delivery. For example, the validation of the fluid delivery event and triggering of the transaction may require receiving a communication originating from a caregiver (such as a doctor) authorizing the fluid delivery to the recipient. In view of such embodiments, one or more record management processing nodes can be configured to: i) receive second input indicating a second event, the second event indicating authorization from a caregiver to administer the fluid delivery via the fluid delivery device; the criteria can be configured to specify that the first event and the second event are required to validate the fluid delivery event and trigger the transaction.

In the event that appropriate criteria are met, the notification of the fluid delivery event from the fluid delivery device triggers a transaction such as payment of fees from the recipient's health care insurance provider to the caregiver on behalf of the recipient. Thus, the communication from the fluid delivery device (i.e., a medical device) triggers the payment transaction.

As previously discussed, the fluid delivery device notifies the first record management-processing node of the fluid delivery event. In accordance with further embodiments, the multiple processing nodes collectively create and/or modify one or more blockchain records to indicate the fluid delivery from the fluid delivery device to the recipient. Accordingly, embodiments herein multiple processing nodes to record the fluid delivery event in a blockchain record.

In accordance with yet further embodiments, the blockchain record can be configured to include the code indicating the criteria. Alternatively, the blockchain record can be configured to include a pointer specifying a remote location in which to obtain the code indicating the criteria.

Embodiments herein are useful over the prior art. For example, notification of a fluid delivery event to a record management resource (such as one or more processing nodes) results in recording of the event as well as triggering of an appropriate transaction (or action) associated with the fluid delivery.

These and other more specific embodiments are disclosed in more detail below.

Note that any of the resources as discussed herein can include one or more computerized devices, fluid delivery device, medical devices, infusion devices, fluid delivery systems, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (such as a physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: receive input indicating a fluid delivery event, the fluid delivery event indicating fluid delivery from a fluid delivery device to a recipient; identify code pertinent to the fluid delivery event, the code including criteria in which to validate the fluid delivery event; apply the criteria to validate the fluid delivery event; and in response to validation of the fluid delivery event based on the criteria in the code, trigger a transaction associated with the fluid delivery event.

The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for efficient delivery fluid to a downstream recipient. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty. For additional details and/or possible perspectives (permutations) of the invention(s), the reader is directed to the Detailed Description section and corresponding figures of the present disclosure as further discussed below.

Figure 1:
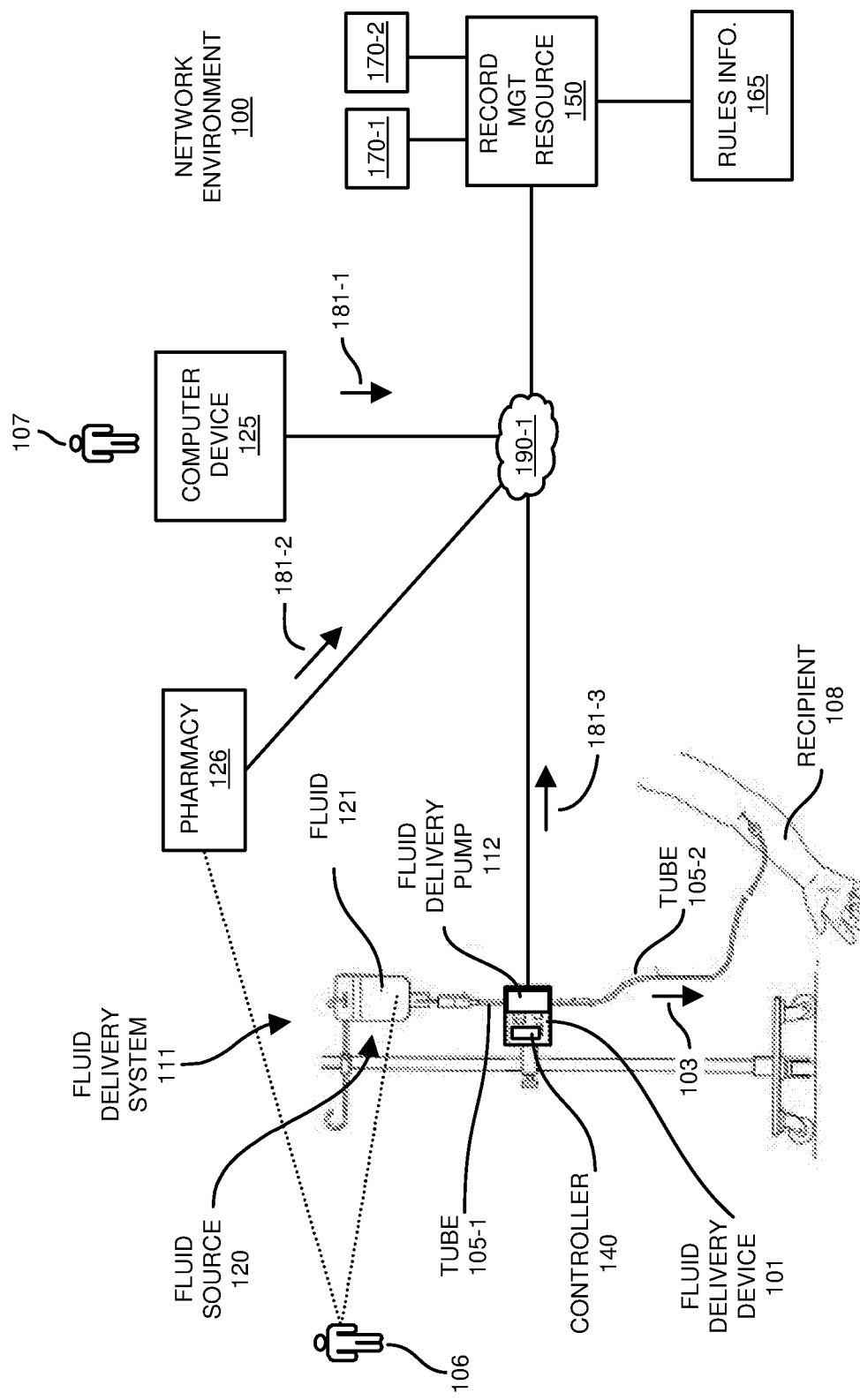
FIG. 1 is an example diagram illustrating a fluid delivery system according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

A network environment includes a fluid delivery device and a remote management resource such as a network of multiple record management processing nodes. The fluid delivery pump is in communication with one or more of the record management-processing nodes in the network. At least a first record management processing node in the network receives input indicating a fluid delivery event associated with the fluid delivery device. In one embodiment, the fluid delivery event indicates fluid delivery from the fluid delivery pump to a recipient. The record management-processing node identifies code (such as rule information or criteria) pertinent to the fluid delivery event; the processing node uses the code and corresponding criteria to validate the fluid delivery event and initiate an appropriate transaction. In response to validation of the fluid delivery event as specified by the criteria in the code, a resource such as the record management-processing node triggers one or more transactions associated with the fluid delivery event.

Now, more specifically, FIG. 1 is an example diagram illustrating a fluid delivery system according to embodiments herein.

As shown, network environment 100 includes caregiver 107 (such as a doctor) that prescribes fluid 121 for delivery to recipient 108. In one embodiment, the caregiver 107 provides notification of the prescribed fluid 121 (for delivery to recipient 108) to computer device 125. Computer device 125 provides notification of the order indicating the prescribed fluid to a pharmacy 126 that supplies the fluid 121 to caregiver 106. In accordance with the prescription (of fluid 121) from the caregiver 107, caregiver 106 obtains or retrieves, from the pharmacy 126, the fluid source 120 and corresponding fluid 121 for delivery to the recipient 108. Via communications 181-1 over network 190-1, the communication device 125 provides notification of the order (prescribed fluid) to the record management resource 150.

In one embodiment, the pharmacy 126 provides notification (via communications 181-2 to record management resource 150) of the caregiver 106 retrieving fluid source 120 and corresponding prescribed fluid 121. For example, the pharmacy 126 transmits communications 181-2 over the network 190-1 to the record management resource 150 indicating that the fluid source 120 and corresponding fluid was supplied to the caregiver 106. Accordingly, the record management resource 150 receives notification of the caregiver 106 obtaining the fluid source 120 and corresponding fluid 121.

As further shown, network environment 100 includes fluid delivery system 111. Fluid delivery system 111 includes fluid delivery device 101, and corresponding tubes 105 (tube 105-1 and tube 105-2). Fluid delivery device 101 includes a controller 140 as well as a corresponding fluid delivery pump 112.

During operation of the fluid delivery pump 112 as controlled by controller 140, and in a manner (such as flow rate, amount, type of fluid, etc.) as specified by the prescription (order) generated by the caregiver 107, the tube 105-1 conveys 121 fluid from the fluid source 120 to the fluid delivery pump 112; tube 105-2 conveys fluid 121 from the fluid delivery pump 112 to the recipient 108. In accordance with control input from the controller 140, the fluid delivery pump 112 delivers the prescribed fluid 121 to the recipient 108 at a rate as indicated by the prescription (such as medication order) generated by the caregiver 107.

Note that the recipient 108 can be a human, patient, delivery site such as in a manufacturing plant, etc.

As further shown in this example embodiment, in addition to pumping fluid 121 to a recipient 108, the fluid delivery device 101 is in communication with remote management resource 150 over network 190-1. In one embodiment, as its name suggests, the remote management resource 150 manages records associated with delivery of the prescribed fluid 121 to the recipient 108.

By further way of non-limiting example, in response to detecting a fluid delivery event such as delivery of fluid 121 to the recipient (such as prescribed by the caregiver 107 or other suitable resource), the controller 140 of the fluid delivery device 101 initiates communications 181-3 over network 190-1 to the remote management resource 150. The communications 181-3 notify the remote management resource 150 of the fluid delivery event associated with the prescribed order issued by the caregiver 107.

Note that the communications 181-1 transmitted from the communication device 125 to the remote management resource 150 can include any suitable information such as a unique identifier value assigned to the caregiver 107, a unique identifier value assigned to recipient 108, details of the fluid to be delivered to the recipient 108, amount of fluid, duration of delivering fluid, amount of delivered fluid, prescription order information, etc., and so on.

Note that the communications 181-2 transmitted from the communication device 125 to the remote management resource 150 can include any suitable information such as a unique identifier value assigned to the caregiver 106 retrieving the fluid 121, a unique identifier value assigned to recipient 108 to receive the fluid 121, details of the fluid 121 to be delivered to the recipient 108, amount of fluid, duration of delivering fluid, amount of delivered fluid, prescription order information, etc., and so on.

Note that the communications 181-3 transmitted from the fluid delivery device 101 to the remote management resource 150 can include any suitable information such as a unique identifier value assigned to the fluid delivery device 101, a unique identifier value assigned to recipient 108, details of the fluid delivery event (such as type of fluid delivered, amount of fluid, duration of delivering fluid, amount of delivered fluid, prescription order information, caregiver prescribing the fluid, etc.), and so on.

Accordingly, via communications 181-1, 181-2, 181-3, etc., the remote management resource 150 receives notification of events such as a fluid order event (communication 181-1) by caregiver 107, pickup of fluid source 120 (fluid 121) from the pharmacy by caregiver 106 (via communications 181-2), and delivery of the fluid 121 to the recipient 108 (via communications 181-3).

As further described herein, in one embodiment, the remote management resource 150 can be configured to apply criteria such as rule information 165 to the received communications 181. When the communications 181 satisfy criteria as specified by the rule information 165, the remote management resource 150 initiates one or more transactions such as between entities 170 (such as entity 170-1, entity 170-2, etc.) based on the events that have been detected.

Figure 2:
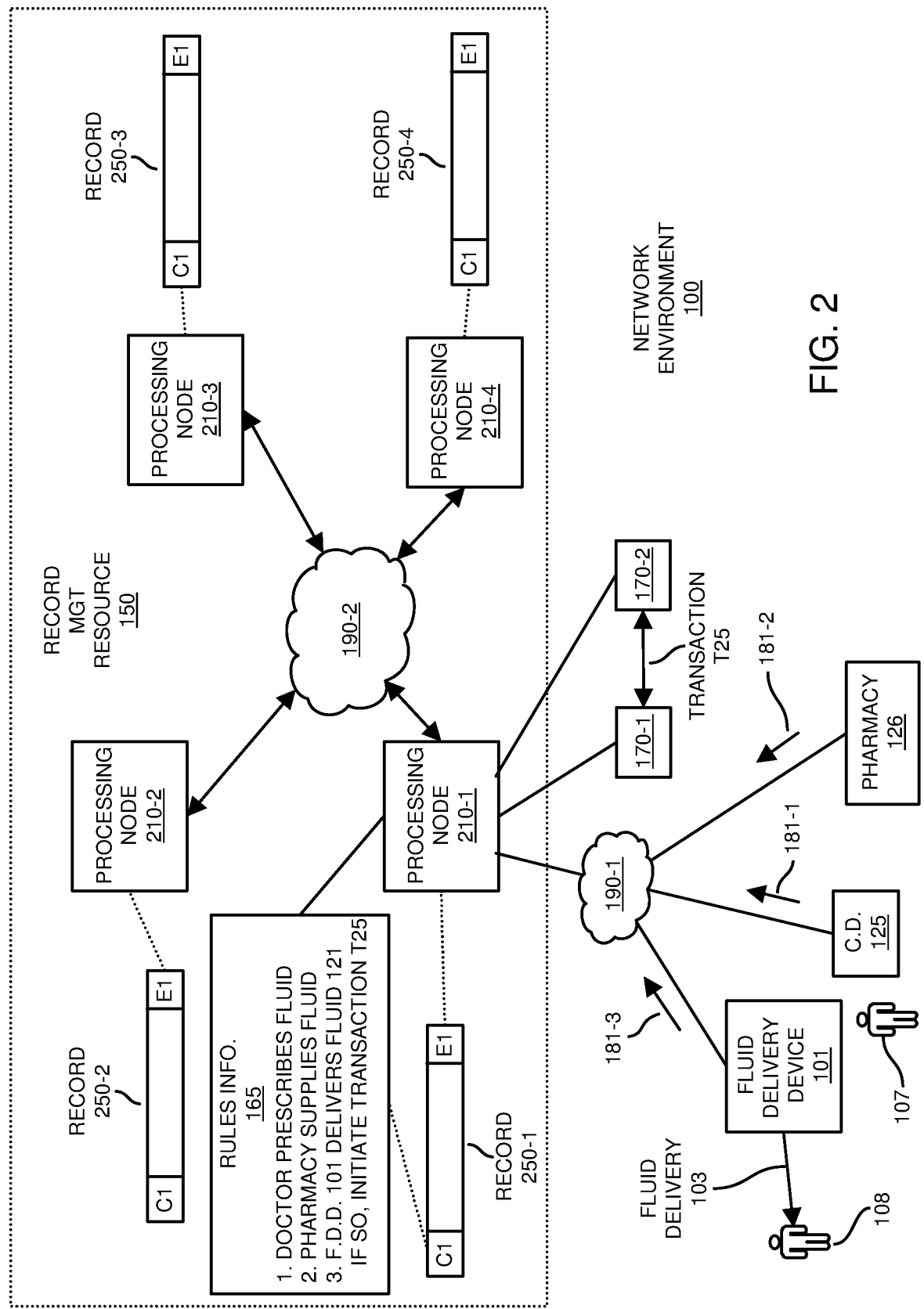
FIG. 2 is an example diagram illustrating fluid delivery record management and transaction initiation according to embodiments herein.

FIG. 2 is an example diagram illustrating fluid delivery setting information facilitating delivery of one or more fluids to a recipient according to embodiments herein.

In this example embodiment, network environment 100 includes remote management resource 150. Record management resource 150 includes multiple processing nodes 210-1, 210-2, 210-3, etc., each of which generates an identical record of events associated with fluid delivery 103 to a target recipient 108.

In one embodiment, each of the records 250 is a blockchain record. Further in this example embodiment, processing node 210-1 processes record 250-1; processing node 210-2 processes record 250-2; processing node 210-3 processes record 250-3; so on.

Assume that the first processing node 210-1 in the network environment 100 receives notification 181-3 of a fluid delivery event from the fluid delivery device 101 (medical device). The fluid delivery event as specified by the notification 181-3 indicates an event, E1, such as that a prescribed fluid 121 has been delivered to a respective target recipient 108. Note that E1 can be any type of event.

In response to receiving communication 181-3 and notification of the event, E1, the first processing node 210-1 communicates with the other processing nodes 210-2, 210-3, etc., in the network environment 100 to validate occurrence of the fluid delivery event E1 and update the distributed record 250 at each of the processing nodes 210. Subsequent to validation of the fluid delivery event E1 by the processing nodes 210, each of the processing nodes 210 in the network environment 100 appends a new block (such as corresponding block E1) to their corresponding record to keep track of the newly detected fluid delivery event E1. Thus, the record 250 is updated at multiple processing nodes.

Note that each block in the record can be assigned time stamp information. For example, blocks in the record 250 be time-stamped; events can be timestamped as well. Time-stamping of accepted and validated blocks in the distributed record 250 can be implemented using any suitable record management technology such as blockchain technology.

In one embodiment, timestamping of event records stored in the record may not be stored in the chain in chronological order. In addition to timestamping, each block can be encrypted in a unique manner with respect to each other.

For each newly detected event such as one or more fluid delivery events associated with the fluid delivery device 101, the fluid delivery device 101 communicates a corresponding message over network 190-1 to the first processing node 210-1. In a similar manner as previously discussed, the first processing node 210-1 communicates with the other processing nodes in the network environment 100 to update the distributed record 250-1. In one embodiment, is order to make a change to the record 250-1 processed by the processing node 210-1, each of the other processing nodes 210-2, 201-3, 210-4, etc., must authorize and agree to the change. In this manner, record 250-1, 250-2, 250-3, 250-4, etc., are all copies of each other.

In one embodiment, the record 250 is associated with the recipient 108. For example, via communications 181 from the fluid delivery device 101 or other resources, the processing node 210 receives a unique identifier value associated with the recipient 108 that receives the fluid 121. The processing node 210-1 uses the unique identifier value of the recipient 108 (as indicated by the fluid delivery device 101) to identify the corresponding record 250 to be processed. As previously discussed, the record 250 can be configured to store (medical) information associated with recipient 108.

In accordance with further embodiments, each of the block records can be configured to include code (such as C1) to be executed or used by a respective processing node. In one embodiment, the code (such as criteria, rules, etc.), when executed or applied, monitor a respective block chain record 250 for occurrence of one or more predetermined events. In one embodiment, code C1 includes rule information 165. As previously discussed, rule information 165 can include criteria that must be satisfied is operable to initiate a respective transaction.

Upon detection of an event (or sequence of events) as specified by or applicable to the code (C1), a respective one or more of the processing nodes 210 of record management resource 150 generates a communication such as a notification, flag, message, etc., indicating occurrence of the detected event. In certain instances, upon detecting an event or sequence of events, one or more processing nodes 210 initiates a transaction between one or more entities 170.

For example, as previously discussed, network environment 100 includes a fluid delivery device 101 and a network of multiple processing nodes 210 (associated with record management resource 150) that collectively manage one or more records associated with delivery of fluid to a recipient 108 such as a patient. The fluid delivery device 101 is in communication with one or more record management processing nodes 210 of record management resource 150. The record management-processing nodes 210 can be configured to collectively control updating of a respective one or more records associated with the recipient or fluid delivery event.

Note that the record management resource 150 can be configured to authenticate each of the entities communication device 125, pharmacy 126, fluid delivery device 101, etc. and corresponding communications 181-1, 181-2, 181-3, etc. in order to update a respective record and initiate a transaction.

In one embodiment, as previously discussed, the fluid delivery device 101 establishes a communication link between the fluid delivery device 101 and (at least) a first record management-processing node 210-1. The first record management-processing node 210-1 receives, such as from the fluid delivery device 101 itself or other resource, input indicating a fluid delivery event (such as delivery of fluid 121 to recipient 108) from the fluid delivery device 101.

The fluid delivery event can include any suitable information. For example, in one embodiment, the fluid delivery event indicates an event of delivering fluid (such as fluid 121 prescribed by a doctor) from the fluid delivery device 101 to the recipient 101.

As previously discussed, the notification of the fluid delivery event as transmitted in communications 181-3 to the one or more record management-processing node 210 can include any suitable information such as a globally unique identifier value assigned to the fluid delivery device, a globally unique identifier value assigned to the patient (recipient) receiving the fluid delivery, type of fluid delivered to the recipient, date of delivery, identity of a doctor prescribing the fluid delivery to the recipient, business entity employing the doctor, etc.

The notification of the fluid delivery event (as indicated in communications 181-3 or other communications such as communications 181-1, 181-2, etc.) to the first record management-processing node 210-1 prompts the first record management-processing node 210-1 to identify a record 250 associated with the recipient 108. In accordance with further embodiments, the processing node 210-1 identifies code (such as executable code, instructions, rules, etc.) pertinent to the fluid delivery event. In one embodiment, the one or more processing nodes 210 in the network of processing nodes associated with record management resource 150 are operable to: receive notification of a unique identifier value assigned to the recipient 108; and utilize the unique identifier value of the recipient 108 to obtain the code (such as code C1) applicable to the fluid delivery event.

Note that the code associated with a delivery event can reside in any suitable location. For example, the record 250 can be configured to include a copy of the code C1 indicating the criteria (rules 165). Alternatively, the record 250 can be configured to include a pointer specifying a remote location in which to obtain the code indicating the criteria (rules 165).

Assume in this example that the code C1 associated with the fluid delivery event includes criteria (rules 165) in which to validate the fluid delivery event for possible triggering of a transaction. In one embodiment, in response to validation of the fluid delivery event (such as delivery of fluid 121 to the recipient 108 via the fluid delivery device 101), the first record management-processing node 210-1 triggers an appropriate transaction amongst one or more parties (entities 170) associated with fluid delivery event.

As a more specific example, in one embodiment, the criteria (such as rules 165) may indicate that the transaction (such as payment to an entity employing the caregiver 106 and 107 for administering the delivery of fluid 121) may not take place unless criteria (rules 165) as specified by the code C1 are met. Assume that the criteria (rules 165) require that multiple entities (such as caregiver 107, pharmacy 126, and fluid delivery device 101) associated with the fluid delivery event to recipient 108 each provide appropriate input associated with the fluid delivery.

More specifically, the validation of the fluid delivery event and triggering of the transaction T25 associated with code C1 may require: i) receiving communications 181-1 originating from a caregiver 107 (such as a doctor) authorizing the delivery of fluid 121 to the recipient 108; ii) receiving communications 181-2 originating from a pharmacy 126 indicating supply of fluid 121 to the caregiver 106; iii) receiving communications 181-3 originating from the fluid delivery device 101 indicating delivery of fluid 121 to the recipient 108.

In view of such embodiments, one or more record management processing nodes can be configured to validate the fluid delivery event based on rules information 165 and corresponding criteria. In the event that appropriate criteria are met, the notification of the fluid delivery event from the fluid delivery device 101 to the record management resource 150 triggers a transaction T25 such as payment of fees from the recipient's health care insurance provider (170-1) to the caregiver (170-2) on behalf of the recipient. Thus, the communications 181-3 from the fluid delivery device (i.e., a medical device) triggers the payment transaction T25.

As previously discussed, the fluid delivery device notifies the first record management-processing node of the fluid delivery event. In accordance with further embodiments, the multiple processing nodes collectively create and/or modify one or more blockchain records to indicate the fluid delivery from the fluid delivery device to the recipient 108. Additionally, note that the one or more processing nodes can be configured to update the record 250 to indicate occurrence of the transaction T25. Accordingly, embodiments herein include multiple processing nodes to record the fluid delivery event and initiated transaction in a respective medical record (such as a blockchain record).

Figure 3:
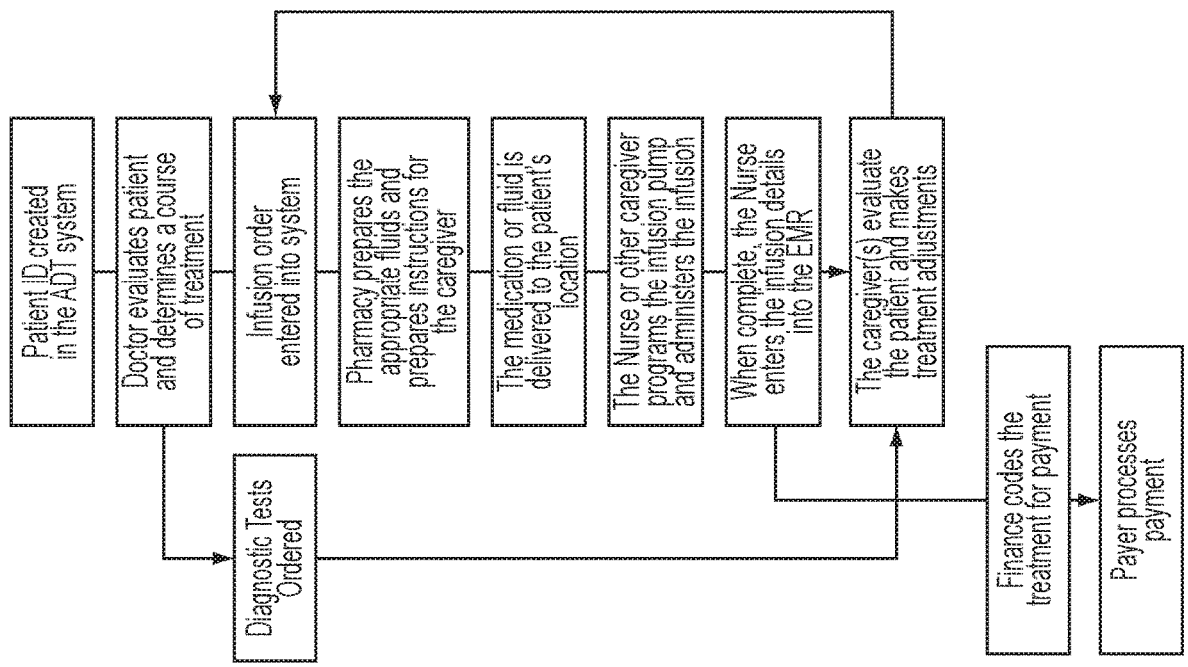
FIG. 3 is an example diagram illustrating a typical infusion order life cycle according to embodiments herein.

FIG. 3 is an example diagram illustrating a typical infusion order life cycle according to embodiments herein.

Many of the processes and workflows in health care depend on sophisticated electro-mechanical devices. Even though there is a wide range of solutions designed to electronically gather, store and automate various types of information and transactions, these systems historically do not communicate and share information effectively. Given the increasing concerns about privacy and security, interoperability is becoming more of a challenge.

Embodiments herein include methods and systems utilizing record management technology (such as blockchain or other suitable technology) to enable a secure, transparent, and immutable transaction record for a medical device and/or corresponding patient. The system as discussed herein can be applied to any electronic medical device but, as discussed above, a fluid delivery pump (or infusion pump) is described as an illustrative example.

Patients in hospitals, infusion clinics or other care settings commonly receive one or more intravenous infusions. These infusions may include medications, antibiotics, blood products or any number of other fluids. The typical workflow for an infusion order follows a sequence of steps, many of which require manual steps.

Referring again to FIGS. 1 and 2, a typical infusion order workflow within a healthcare environment can be outlined as follows:

1. A patient such as recipient 108 is admitted into the healthcare system through a registration process. This process yields a unique patient identifier and sometimes a unique visit identifier. Each transaction and corresponding portion of patient information is associated with one or both of the unique identifier values for the length of the patient's care with that institution.

2. A caregiver 107 such as a doctor evaluates the patient (such as recipient 108) and determines a treatment plan such as delivery of fluid 121.

3. When required, one or more medication or fluids orders are prescribed for the patient using an Order Entry (OE) system.

4. A pharmacist (associated with pharmacy 126) prepares the order received from caregiver 107 and sends the order (fluid 121) to the recipient's location.

5. The caregiver 106 receives the fluid 121 (fluid source 120) and the order details, programs the fluid delivery device 101 according to the order and administers the infusion of fluid 121 to the recipient 108.

6. As the infusion is administered, details of that infusion (fluid delivery event) are documented in the patient's medical record such as record 250. As previously discussed, multiple processing nodes 210 in record management resource 150 collectively manage record 250.

7. During and/or after the infusion is delivered to the recipient 108, the caregiver(s) evaluate the recipient 108 (patient) and, in consideration of that and other information, may adjust the treatment plan.

Figure 4:
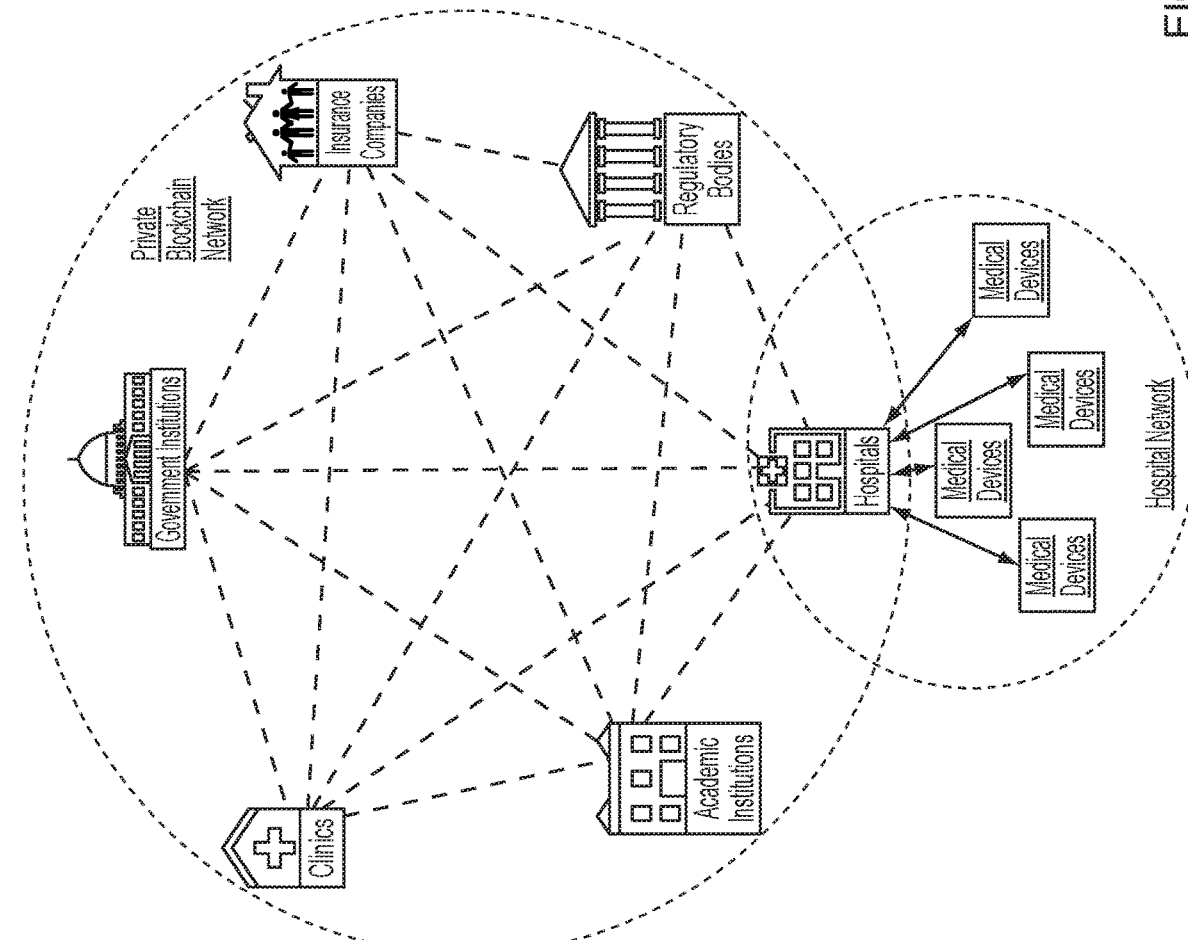
FIG. 4 is an example diagram illustrating a representative semi-private, consortium blockchain network topology according to embodiments herein.

8. If necessary, new orders for new infusions may be entered into the record management resource 150 and the process is repeated FIG. 4 is an example diagram illustrating a representative semi-private, consortium blockchain network topology according to embodiments herein.

As shown, multiple independent institutions, who each play a different part in the healthcare system, are connected via a network such as the Internet. There is no limit to the number or type of independent institutions in the network. The more independent participants, the more robust and secure the system. Each of these participant institutions devote the necessary resources to be one or, in the case of a health insurance company, multiple block chain nodes. The nodes execute the consensus algorithms necessary to validate new blocks and store copy of one or more blockchain networks it is part of. These participants might also be referred to "miners" or "forgers" depending on the type of consensus algorithm employed.

Figure 5:
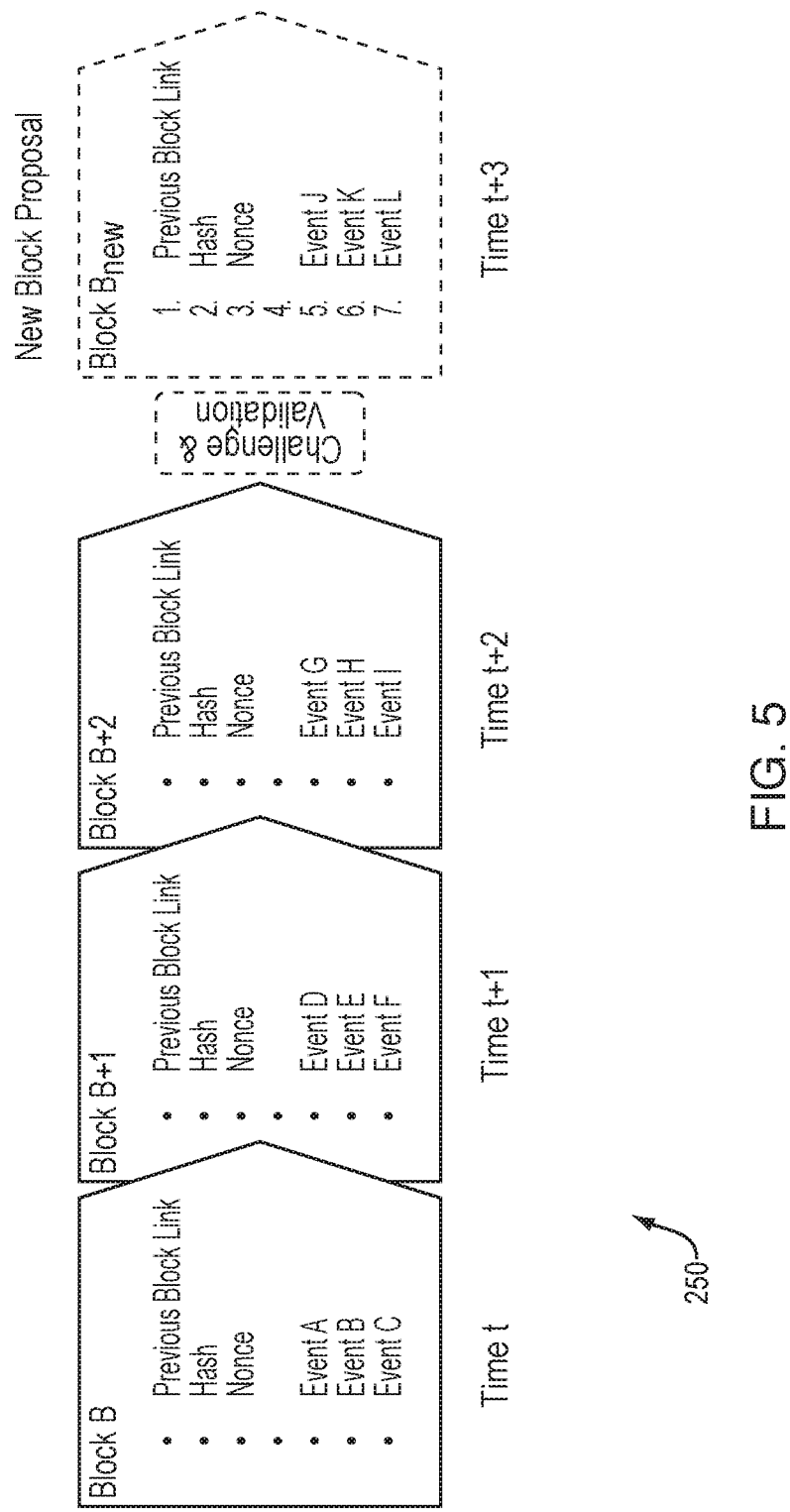
FIG. 5 is an example diagram illustrating a simplified representation of blocks in a block chain according to embodiments herein.

FIG. 5 is an example diagram illustrating a simplified representation of blocks in a block chain according to embodiments herein.

In this example embodiment, a new block added to record 250 indicates occurrence and details associated with one or more events. Accordingly, record 250 can be updated to keep track of any suitable events and/or transaction as previously discussed.

Figure 6:
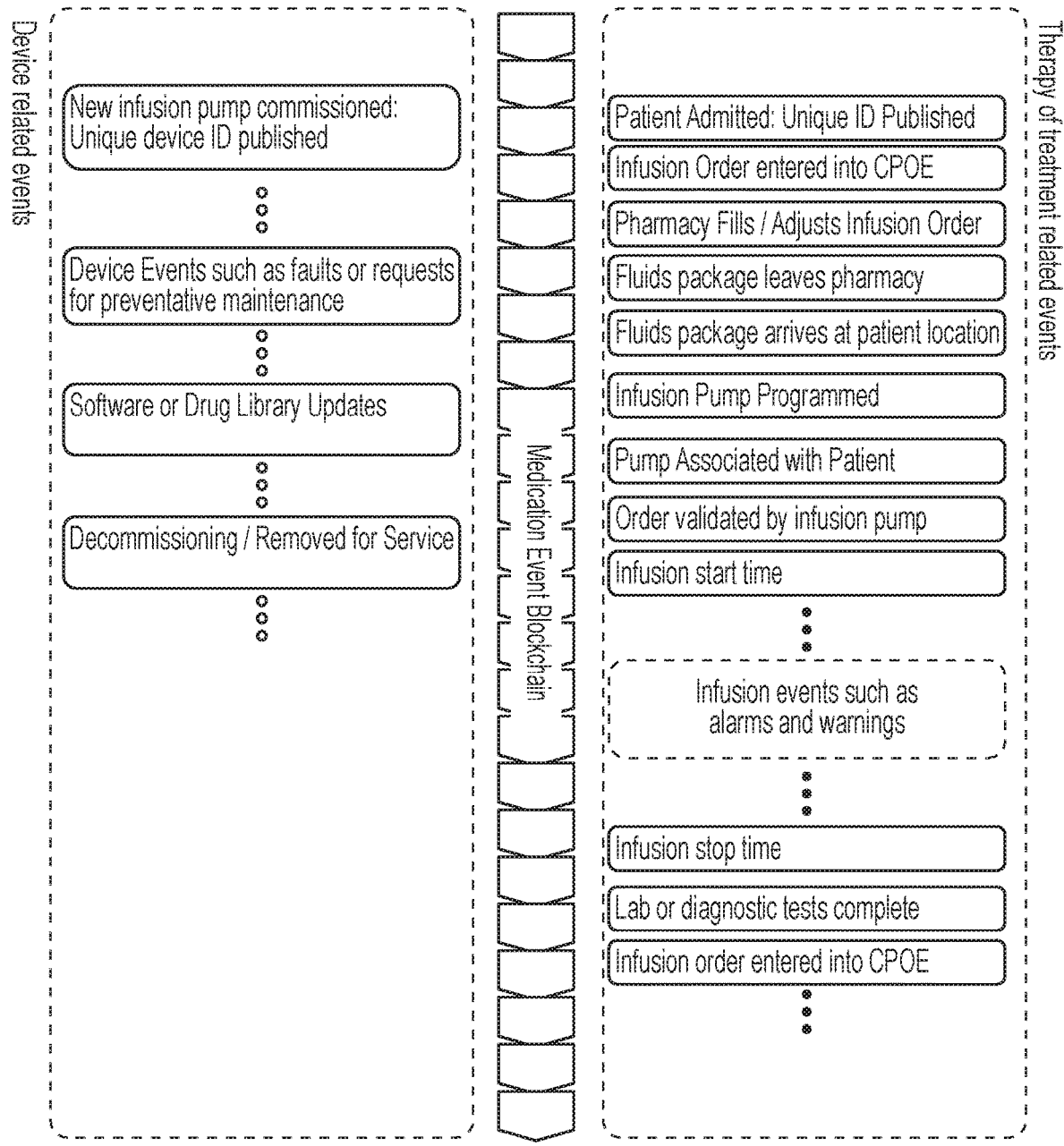
FIG. 6 is an example diagram illustrating a combined view of infusion order events and device events added to a blockchain according to embodiments herein.

FIG. 6 is an example diagram illustrating a combined view of infusion order events and device events added to a blockchain according to embodiments herein.

In this example embodiment, the record 610

Figure 7:
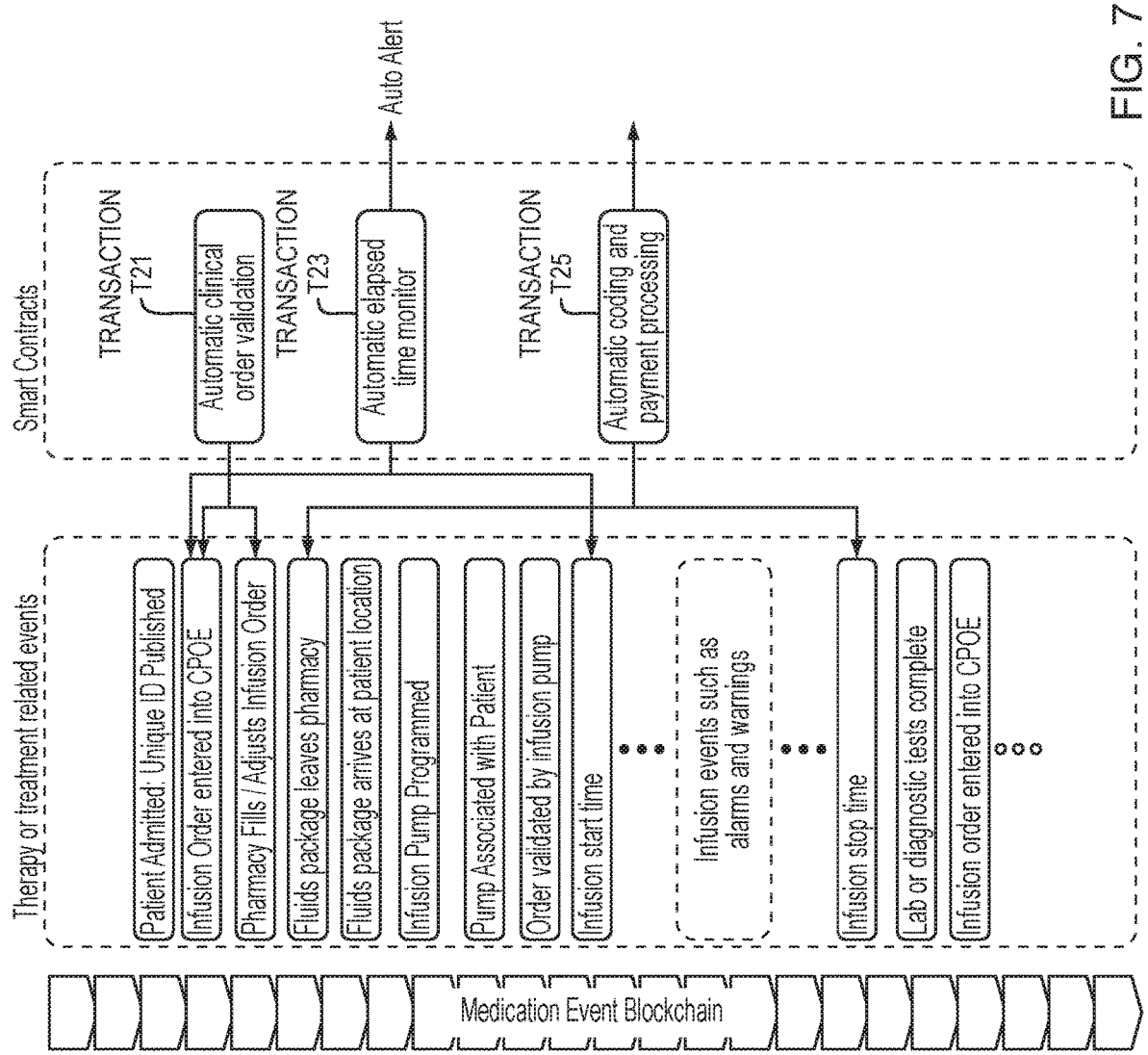
FIG. 7 is an example diagram illustrating "smart contracts" embedded in a blockchain that can be programmed to trigger transactions based on various steps in an infusion workflow according to embodiments herein.

FIG. 7 is an example diagram illustrating "smart contracts" embedded in a blockchain record that can be programmed to trigger transactions based on various steps in an infusion workflow according to embodiments herein.

In one embodiment, the code (such as code C1 or contracts) stored in a respective blockchain record is executable code. In a manner as previously discussed, execution of the code by one or more processing nodes results in processes such as inspection of block chain events, recording of additional events, triggering of external events, transactions, notifications, alarms, or other types of "off-chain" communications. In other words, when a certain event or group of events is detected by executed code in the record, the corresponding one or more processing nodes associated with record management resource 150 initiates execution of a respective transaction such as T25, respective notification such as N23, execution of a respective process such as P17, etc.

Figure 8:
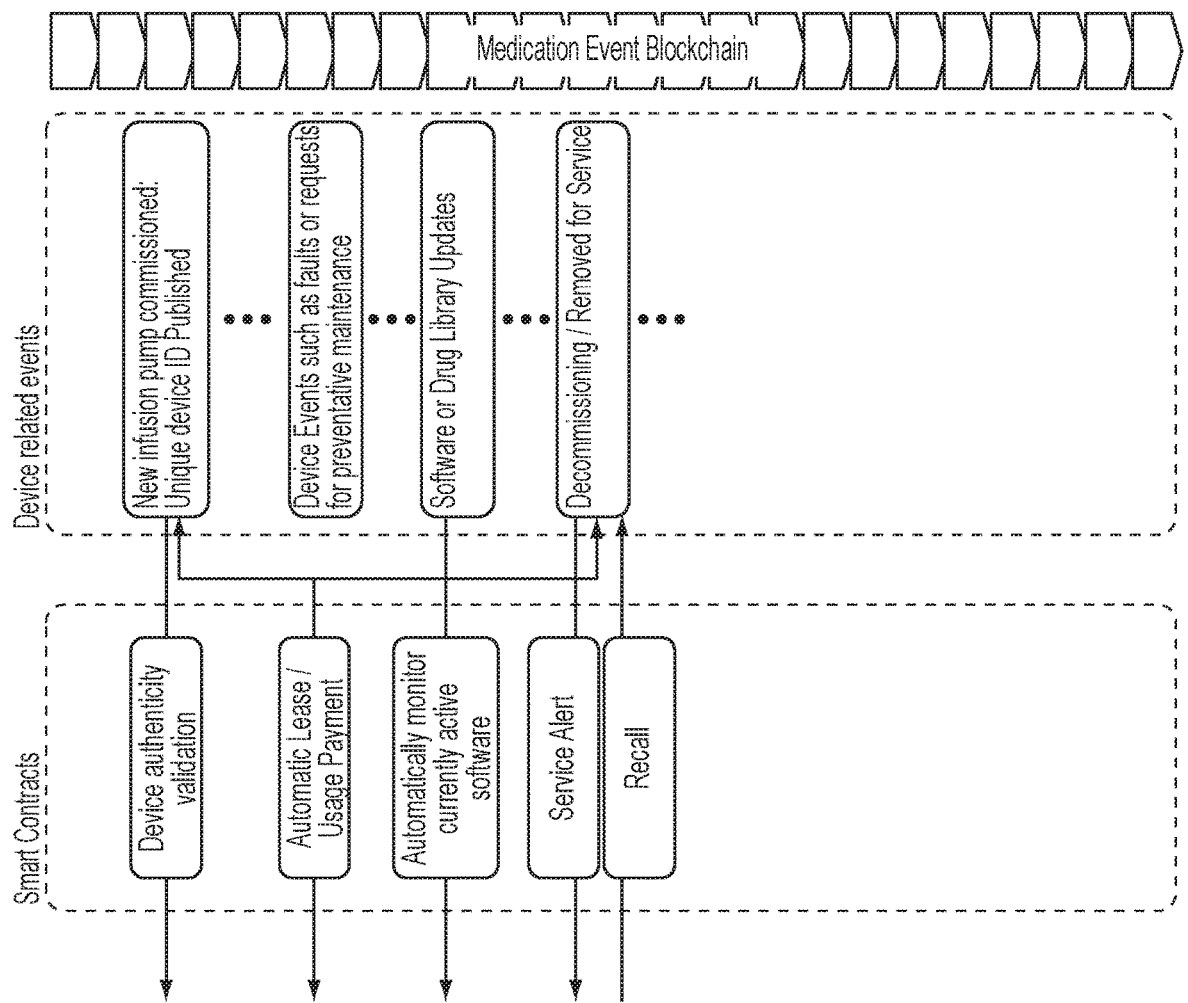
FIG. 8 is an example diagram illustrating one or more contracts embedded in a blockchain according to embodiments herein.

FIG. 8 is an example diagram illustrating one or more contracts embedded in a blockchain according to embodiments herein.

These algorithms used to inspect block chain events can be used to recorded additional events or trigger external events, notifications, alarms, or other types of "off-chain" communications.

Figure 9:
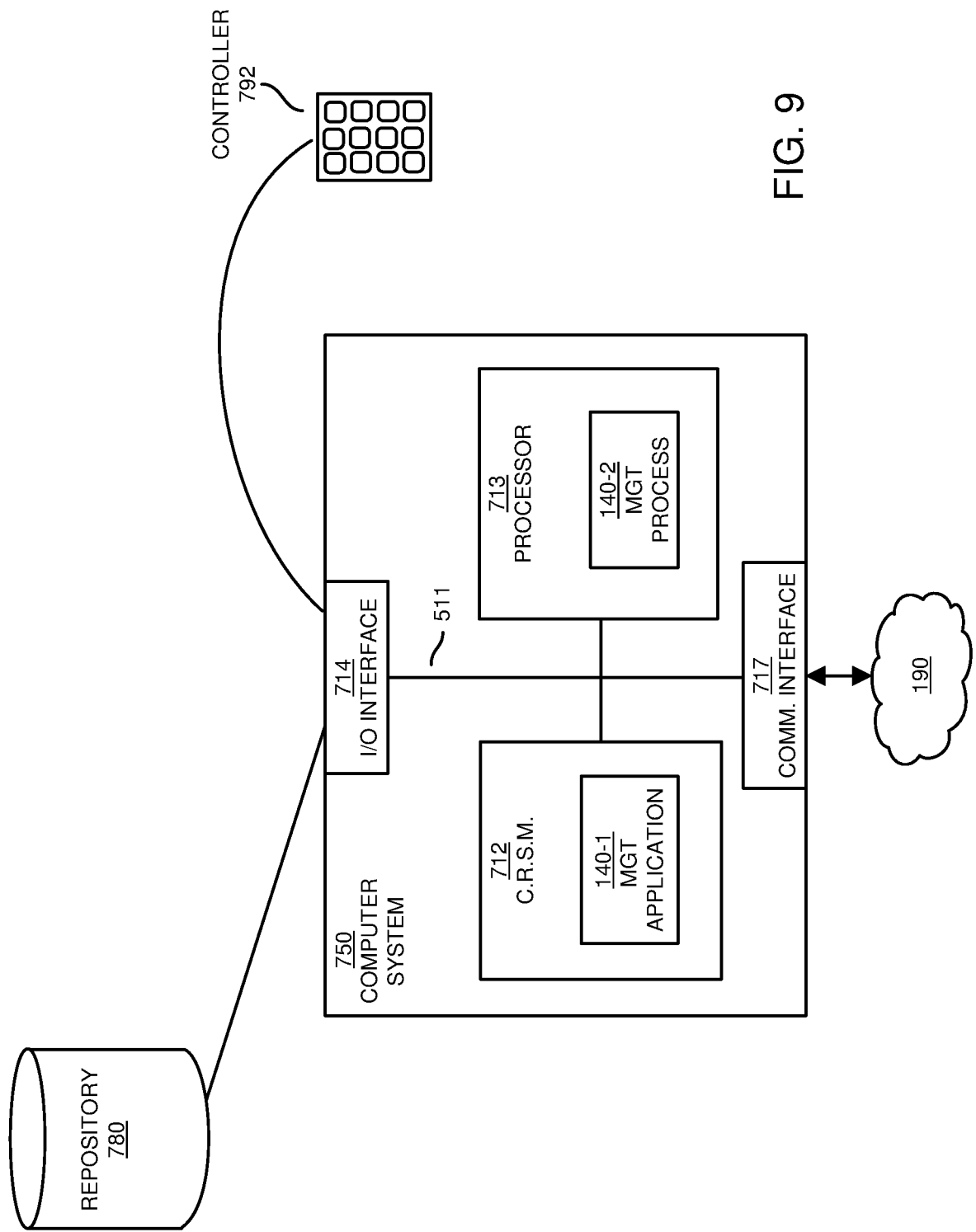
FIG. 9 is an example diagram illustrating a computer system in which to execute any of the functionality according to embodiments herein.

FIG. 9 is an example block diagram of a computer system for implementing any of the operations as discussed herein according to embodiments herein.

Any of the resources (such as controller 140, fluid delivery system 111, record management resource 150, etc.) as discussed herein can be configured to include computer processor hardware and executable instructions to carry out any of the corresponding operations as discussed herein.

As shown, computer system 950 of the present example includes an interconnect 911 coupling computer readable storage media 912 such as a non-transitory type of media (such as a hardware storage medium) in which digital information can be stored and retrieved, a processor 913 (computer processor hardware), I/O interface 914, and a communications interface 917. I/O interface 914 supports connectivity to repository 980 and input resource 992.

Computer readable storage medium 912 (hardware to store instructions) can be any hardware storage device such as memory, optical storage, hard drive, floppy disk, etc. In one embodiment, the computer readable storage medium 912 stores instructions and/or data.

As shown, computer readable storage media 912 can be encoded with control application 140-1 (e.g., including instructions) associated with controller 140 to carry out any of the operations as discussed herein.

During operation of one embodiment, processor 913 accesses computer readable storage media 912 via the use of interconnect 911 in order to launch, run, execute, interpret or otherwise perform the instructions in management application 140-1 stored on computer readable storage medium 912. Execution of the management application 140-1 produces management process 140-2 to carry out any of the operations and/or processes as discussed herein associated with record management resource 150, controller 140, fluid delivery device 101, etc.

Those skilled in the art will understand that the computer system 950 can include other processes and/or software and hardware components, such as an operating system that controls allocation and use of hardware resources to execute management application 140-1.

In accordance with different embodiments, note that computer system may be or included in any of various types of devices, including, but not limited to, a medical device, a fluid delivery pump, fluid delivery system, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, set-top box, content management device, handheld remote control device, any type of computing or electronic device, etc. The computer system 950 may reside at any location or can be included in any suitable resource in any network environment to implement functionality as discussed herein.

Functionality supported by the different resources will now be discussed via flowcharts in FIG. 10. Note that the steps in the flowcharts below can be executed in any suitable order.

Figure 10:
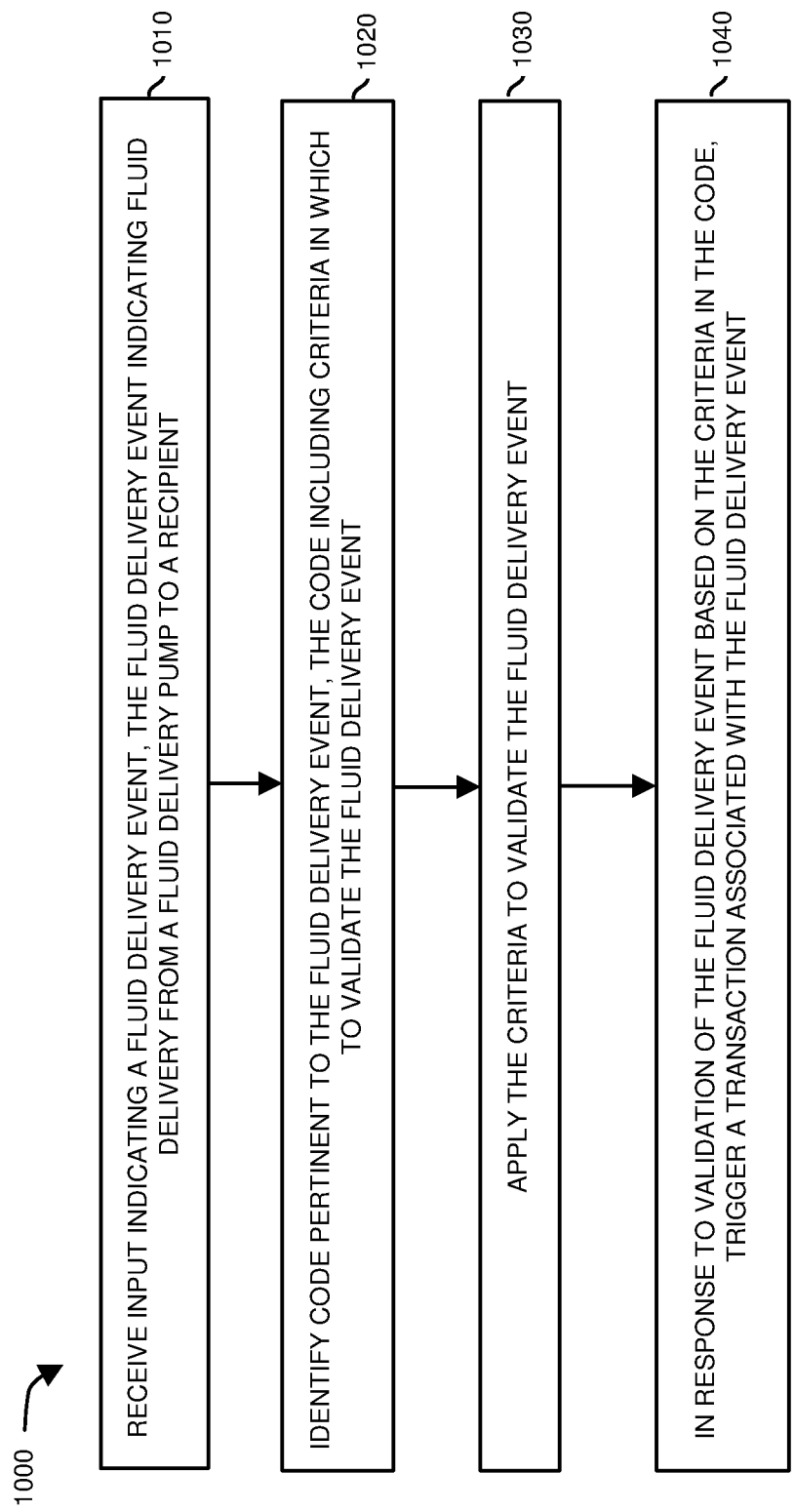
FIG. 10 is an example diagram illustrating a method according to embodiments herein.

FIG. 10 is a flowchart 1000 illustrating an example method according to embodiments. Note that there will be some overlap with respect to concepts as discussed above.

In processing operation 1010, the remote (record) management resource 150 (such as processing node 210-1) receives input 102 indicating a fluid delivery event. The fluid delivery event 102 indicates fluid delivery from a fluid delivery device 101 to a recipient 108.

In processing operation 1020, the remote (record) management resource 150 (such as processing node 210-1) identifies code pertinent to the fluid delivery event as specified by the input 102. The code includes criteria in which to validate the fluid delivery event.

In processing operation 1030, the remote (record) management resource 150 (such as processing node 210-1) applies the criteria to validate the fluid delivery event.

In processing operation 1040, in response to validation of the fluid delivery event based on the criteria in the code, the remote (record) management resource 150 (such as processing node 210-1) triggers a transaction associated with the fluid delivery event.

Note again that techniques herein are well suited for managing records associated with providing healthcare to a recipient. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A system comprising:
    a first record management processing node in a network of multiple record management processing nodes, the first record management processing node in communication with a fluid delivery device, the first record management processing node operable to:
        receive input indicating a fluid delivery event, the fluid delivery event indicating delivery of fluid from the fluid delivery device to a recipient as administered by a caregiver;
        update a blockchain record associated with the recipient to indicate the fluid delivery event and an identity of the caregiver;
        identify code pertinent to the fluid delivery event, the code indicating criteria in which to validate the fluid delivery event;
        trigger a transaction in response to validation of the fluid delivery event as specified by the criteria in the code; and
        wherein the transaction includes payment of a fee to the caregiver operating the fluid delivery device to deliver the fluid, the first record management processing node further operable to:
    update the blockchain record to indicate the transaction.

2. The system as in claim 1, wherein the multiple processing nodes are further operable to: receive the input indicating the fluid delivery event and collectively update the blockchain record associated with the recipient.

3. The system as in claim 1, wherein the validation of the fluid delivery event includes receiving a communication originating from the caregiver authorizing the delivery of fluid.

4. The system as in claim 1, wherein the multiple processing nodes are further operable to: record the fluid delivery event in the blockchain record.

5. The system as in claim 4, wherein the blockchain record includes the code indicating the criteria.

6. The system as in claim 4, wherein the blockchain record specifies a location of the code indicating the criteria.

7. The system as in claim 1, wherein the multiple processing nodes are further operable to:
    receive notification of a unique identifier value assigned to the recipient; and
    utilize the unique identifier value to obtain, from the blockchain record, the code applicable to the fluid delivery event.

8. The system as in claim 1, wherein the network of record management processing nodes includes a second record management processing node, the second record management processing node operable to:
    receive the input indicating the fluid delivery from the fluid delivery device to the recipient;
    identify the code pertinent to the fluid delivery; and
    in parallel with the first processing node, validate the fluid delivery event based on the criteria.

9. The system as in claim 1, wherein the fluid delivery event is a first event, the first record management processing node further operable to:
    receive second input indicating a second event, the second event indicating authorization from the caregiver to administer the delivery of fluid via the fluid delivery device; and wherein the criteria specifies that the first event and the second event are required to validate the fluid delivery event and trigger the transaction.

10. A method comprising:
receiving input indicating a fluid delivery event, the fluid delivery event indicating delivery of fluid from a fluid delivery device to a recipient as administered by a caregiver;
updating a blockchain record associated with the recipient to indicate the fluid delivery event and an identity of the caregiver;
identifying code pertinent to the fluid delivery event, the code indicating criteria in which to validate the fluid delivery event;
applying the criteria to validate the fluid delivery event;
in response to validation of the fluid delivery event based on the criteria in the code, triggering a transaction associated with the fluid delivery event; and
wherein the transaction includes payment of a fee to the caregiver operating the fluid delivery device to deliver the fluid, the method further comprising: updating the blockchain record to indicate the transaction.

11. The method as in claim 10 further comprising:
receiving the input indicating the fluid delivery event from the fluid delivery device.

12. The method as in claim 10 further comprising:
receiving a communication originating from the caregiver, the communication indicating authorization of the delivery of fluid.

13. The method as in claim 10 further comprising:
recording the fluid delivery event in the blockchain record.

14. The method as in claim 13, wherein the blockchain record includes the code indicating the criteria.

15. The method as in claim 13, wherein the blockchain record includes a pointer specifying a location of the code indicating the criteria.

16. The method as in claim 10 further comprising:
receiving notification of a unique identifier value assigned to the recipient; and
utilizing the unique identifier value to obtain the code including the criteria applicable to the fluid delivery event.

17. The method as in claim 10 further comprising:
recording occurrence of the fluid delivery event and transaction in the blockchain record at each of multiple record management processing nodes in a network.

18. The method as in claim 10, wherein the fluid delivery event is a first event, the method further comprising:
receiving notification of a second event indicating authorization from the caregiver to administer the fluid delivery to the recipient via the fluid delivery device; and
wherein the criteria specifies that the first event and the second event are required to validate the fluid delivery event and trigger the transaction, the transaction being between the recipient and the caregiver.

19. Computer-readable storage hardware having instructions stored thereon for execution, such that the instructions, when executed by computer processor hardware, cause the computer processor hardware to:
receive input indicating a fluid delivery event, the fluid delivery event indicating delivery of fluid from a fluid delivery device to a recipient as administered by a caregiver;
update a block chain record associated with the recipient to indicate the fluid delivery event and an identity of the caregiver;
identify code pertinent to the fluid delivery event, the code including criteria in which to validate the fluid delivery event;
generate a notification in response to validation of the fluid delivery event as specified by the criteria in the code; and
wherein the transaction includes payment of a fee to the caregiver operating the fluid delivery device to deliver the fluid, the computer processor hardware further operative to: update the blockchain record to indicate the transaction.

20. The system as in claim 9, wherein the transaction includes payment to the caregiver for administering the delivery of fluid to the recipient.

21. The system as in claim 1, wherein the code is obtained from the blockchain record associated with the recipient.

22. The system as in claim 1, wherein the input indicating the fluid delivery event originates from the fluid delivery device.

23. The system as in claim 1, wherein the validation of the fluid delivery event as specified by the code requires receipt of i) first communications originating from the caregiver authorizing the delivery of fluid to the recipient; ii) second communications originating from a pharmacy indicating supply of the fluid to the caregiver; iii) third communications from the fluid delivery device indicating delivery of the fluid to the recipient.

24. The system as in claim 1, wherein validation of the fluid delivery event includes implementing a monitor to monitor elapsed time between multiple events captured in a treatment log of the blockchain record, the treatment log associated with the fluid delivery event.

* * * * *